(12) United States Patent
Goessl

(10) Patent No.: US 8,940,335 B2
(45) Date of Patent: Jan. 27, 2015

(54) PROCESS FOR MAKING DRY AND STABLE HEMOSTATIC COMPOSITIONS

(75) Inventor: Andreas Goessl, Vienna (AT)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 116 days.

(21) Appl. No.: 13/150,902

(22) Filed: Jun. 1, 2011

(65) Prior Publication Data

US 2012/0021058 A1 Jan. 26, 2012

Related U.S. Application Data

(60) Provisional application No. 61/350,237, filed on Jun. 1, 2010.

(51) Int. Cl.
| | |
|---|---|
| A61K 9/16 | (2006.01) |
| A61K 38/48 | (2006.01) |
| B67C 3/22 | (2006.01) |
| A61K 9/14 | (2006.01) |
| A61L 26/00 | (2006.01) |

(52) U.S. Cl.
CPC ............... *A61K 9/146* (2013.01); *A61K 9/1658* (2013.01); *A61L 26/0038* (2013.01); *A61L 2400/04* (2013.01)
USPC .......................... 424/492; 424/491; 424/94.64

(58) Field of Classification Search
USPC ....................................... 424/94.64, 484, 498
See application file for complete search history.

(56) References Cited

U.S. PATENT DOCUMENTS

| | | | |
|---|---|---|---|
| 2,507,244 A | 5/1950 | Correll | |
| 2,558,395 A | 6/1951 | Studer | |
| 3,089,815 A | 5/1963 | Kupelwieser et al. | |
| 4,006,220 A | 2/1977 | Gottlieb | |
| 4,013,078 A | 3/1977 | Field | |
| 4,124,705 A | 11/1978 | Rothman et al. | |
| 4,164,559 A | 8/1979 | Miyata et al. | |
| 4,179,400 A | 12/1979 | Tsao et al. | |
| 4,265,233 A | 5/1981 | Sugitachi et al. | |
| 4,291,013 A | 9/1981 | Wahlig et al. | |
| 4,292,972 A | 10/1981 | Pawelchak et al. | |
| 4,298,598 A | 11/1981 | Schwarz et al. | |
| 4,300,494 A | 11/1981 | Graiff et al. | |
| 4,347,234 A | 8/1982 | Wahlig et al. | |
| 4,362,567 A | 12/1982 | Schwarz et al. | |
| 4,377,572 A | 3/1983 | Schwarz et al. | |
| 4,424,208 A | 1/1984 | Wallace et al. | |
| 4,453,939 A | 6/1984 | Zimmerman et al. | |
| 4,482,386 A | 11/1984 | Wittwer et al. | |
| 4,515,637 A | 5/1985 | Cioca | |
| 4,536,387 A | 8/1985 | Sakamoto et al. | |
| 4,540,410 A | 9/1985 | Wood et al. | |
| 4,543,332 A | 9/1985 | Jao et al. | |
| 4,554,156 A | 11/1985 | Fischer | |
| 4,600,574 A | 7/1986 | Lindner et al. | |
| 4,640,834 A | 2/1987 | Eibl et al. | |
| 4,655,211 A | 4/1987 | Sakamoto et al. | |
| 4,746,514 A | 5/1988 | Warne | |
| 4,749,689 A | 6/1988 | Miyata et al. | |
| 4,752,466 A | 6/1988 | Saferstein et al. | |
| 4,803,075 A | 2/1989 | Wallace et al. | |
| 4,818,517 A | 4/1989 | Kwee et al. | |
| 4,832,686 A | 5/1989 | Anderson | |
| 4,837,285 A | 6/1989 | Berg et al. | |
| 4,885,161 A | 12/1989 | Cornell | |
| 4,891,359 A | 1/1990 | Saferstein et al. | |
| 4,925,677 A | 5/1990 | Feijen | |
| 4,946,870 A | 8/1990 | Partain, III et al. | |
| 4,950,699 A * | 8/1990 | Holman | 424/448 |
| 5,007,916 A | 4/1991 | Linsky et al. | |
| 5,017,229 A | 5/1991 | Burns et al. | |
| 5,023,082 A | 6/1991 | Friedman et al. | |
| 5,041,292 A | 8/1991 | Feijen | |
| 5,061,274 A | 10/1991 | Kensey | |
| 5,061,492 A | 10/1991 | Okada et al. | |
| 5,080,893 A | 1/1992 | Goldberg et al. | |

(Continued)

FOREIGN PATENT DOCUMENTS

| | | |
|---|---|---|
| CN | 1270240 A | 10/2000 |
| EP | 0132983 A | 2/1985 |

(Continued)

OTHER PUBLICATIONS

Christensen et al., "Qualitative Description of the Wurster-Based Fluid-Bed Coating Process." Drug Development and Industrial Pharmacy, 23(5), 451-463 (1997).*
International Search Report for PCT/EP2011/059062 mailed Nov. 24, 2011, 22 pages.
International Search Report for PCT/EP2011/059065 mailed Nov. 24, 2011, 22 pages.
International Search Report for PCT/EP2011/059114 mailed Nov. 24, 2011, 26 pages.
Ansell et al., "Gelfoam and Autologous Clot Embolization: Effect on Coagulation", *Invest. Radiol.* (1978) 13:115-120.
Barrow, D.L., et al.; "The Use of Greater Omentum Vascularized Free Flaps for Neurosurgical Disorders Requiring Reconstruction"; J. Neurosurg.; vol. 60; pp. 305-311 (Feb. 1984).

(Continued)

*Primary Examiner* — Walter Webb
(74) *Attorney, Agent, or Firm* — Kilpatrick Townsend & Stockton LLP

(57) ABSTRACT

Described is a process for making a dry and stable hemostatic composition, said process comprising
a) providing a dry granular preparation of a biocompatible polymer suitable for use in hemostasis,
b) coating the granules in said dry granular preparation with a preparation of a coagulation inducing agent, thereby obtaining coagulation inducing agent coated polymer granules,
c) filling said coagulation inducing agent coated polymer granules into a final container,
d) finishing the final container to a storable pharmaceutical device containing said coagulation inducing agent coated polymer granules as a dry and stable hemostatic composition.

19 Claims, 2 Drawing Sheets

(56) References Cited

U.S. PATENT DOCUMENTS

| | | | |
|---|---|---|---|
| 5,108,421 A | 4/1992 | Fowler | |
| 5,126,141 A | 6/1992 | Henry | |
| 5,129,882 A | 7/1992 | Weldon et al. | |
| 5,134,229 A | 7/1992 | Saferstein et al. | |
| 5,135,751 A | 8/1992 | Henry et al. | |
| 5,135,755 A | 8/1992 | Czech et al. | |
| 5,140,016 A | 8/1992 | Goldberg et al. | |
| 5,149,540 A | 9/1992 | Kunihiro | |
| 5,162,430 A | 11/1992 | Rhee et al. | |
| 5,165,938 A | 11/1992 | Knighton | |
| 5,178,883 A | 1/1993 | Knighton | |
| 5,192,300 A | 3/1993 | Fowler | |
| 5,196,185 A | 3/1993 | Silver et al. | |
| 5,204,382 A | 4/1993 | Wallace et al. | |
| 5,209,776 A | 5/1993 | Bass et al. | |
| 5,219,328 A | 6/1993 | Morse et al. | |
| 5,275,616 A | 1/1994 | Fowler | |
| 5,292,362 A | 3/1994 | Bass et al. | |
| 5,300,494 A | 4/1994 | Brode, II et al. | |
| 5,304,377 A | 4/1994 | Yamada et al. | |
| 5,306,501 A | 4/1994 | Viegas et al. | |
| 5,324,775 A | 6/1994 | Rhee et al. | |
| 5,328,955 A | 7/1994 | Rhee et al. | |
| 5,330,446 A | 7/1994 | Weldon et al. | |
| 5,350,573 A | 9/1994 | Goldberg et al. | |
| 5,352,715 A | 10/1994 | Wallace et al. | |
| 5,356,614 A | 10/1994 | Sharma | |
| 5,384,333 A | 1/1995 | Davis et al. | |
| 5,385,606 A | 1/1995 | Kowanko | |
| 5,399,361 A | 3/1995 | Song et al. | |
| 5,418,222 A | 5/1995 | Song et al. | |
| 5,428,022 A | 6/1995 | Palefsky et al. | |
| 5,428,024 A | 6/1995 | Chu et al. | |
| 5,437,672 A | 8/1995 | Allyne | |
| 5,447,966 A | 9/1995 | Hermes et al. | |
| 5,478,352 A | 12/1995 | Fowler | |
| 5,507,744 A | 4/1996 | Tay et al. | |
| 5,510,418 A | 4/1996 | Rhee et al. | |
| 5,512,301 A | 4/1996 | Song et al. | |
| 5,514,379 A | 5/1996 | Weissleder et al. | |
| 5,516,532 A | 5/1996 | Atala et al. | |
| 5,520,925 A | 5/1996 | Maser | |
| 5,531,759 A | 7/1996 | Kensey et al. | |
| 5,540,715 A | 7/1996 | Katsaros et al. | |
| 5,580,923 A | 12/1996 | Yeung et al. | |
| 5,595,735 A | 1/1997 | Saferstein et al. | |
| 5,614,587 A | 3/1997 | Rhee et al. | |
| 5,618,551 A | 4/1997 | Tardy et al. | |
| 5,648,506 A | 7/1997 | Desai et al. | |
| 5,658,592 A | 8/1997 | Tanihara et al. | |
| 5,667,839 A | 9/1997 | Berg | |
| 5,672,336 A | 9/1997 | Sharma | |
| 5,674,275 A | 10/1997 | Tang et al. | |
| 5,690,675 A | 11/1997 | Sawyer et al. | |
| 5,698,213 A | 12/1997 | Jamiolkowski et al. | |
| 5,714,370 A | 2/1998 | Eibl et al. | |
| 5,752,974 A | 5/1998 | Rhee et al. | |
| 5,770,229 A | 6/1998 | Tanihara et al. | |
| 5,853,749 A | 12/1998 | Hobbs | |
| 5,856,356 A | 1/1999 | Tsouderos et al. | |
| 5,861,043 A | 1/1999 | Carn | |
| 5,874,500 A | 2/1999 | Rhee et al. | |
| 5,902,832 A | 5/1999 | Van Bladel et al. | |
| 5,908,054 A | 6/1999 | Safabash et al. | |
| 5,931,165 A | 8/1999 | Reich et al. | |
| 5,997,895 A | 12/1999 | Narotam et al. | |
| 6,063,061 A | 5/2000 | Wallace et al. | |
| 6,066,325 A | 5/2000 | Wallace et al. | |
| 6,096,309 A | 8/2000 | Prior et al. | |
| 6,110,484 A | 8/2000 | Sierra | |
| 6,129,761 A | 10/2000 | Hubbell | |
| 6,132,759 A | 10/2000 | Schacht et al. | |
| 6,166,130 A | 12/2000 | Rhee et al. | |
| 6,179,872 B1 | 1/2001 | Bell et al. | |
| 6,277,394 B1 | 8/2001 | Sierra | |
| 6,312,474 B1 | 11/2001 | Francis et al. | |
| 6,312,725 B1 | 11/2001 | Wallace et al. | |
| 6,328,229 B1 | 12/2001 | Duronio et al. | |
| 6,391,343 B1 | 5/2002 | Yen | |
| 6,458,386 B1 | 10/2002 | Schacht et al. | |
| 6,458,889 B1 | 10/2002 | Trollsas | |
| 6,495,127 B1 | 12/2002 | Wallace et al. | |
| 6,624,245 B2 | 9/2003 | Wallace et al. | |
| 6,649,162 B1 | 11/2003 | Biering et al. | |
| 6,706,690 B2 | 3/2004 | Reich et al. | |
| 7,320,962 B2 | 1/2008 | Reich et al. | |
| 7,435,425 B2 | 10/2008 | Qian et al. | |
| 7,547,446 B2 | 6/2009 | Qian et al. | |
| 7,871,637 B2 | 1/2011 | Qian et al. | |
| 8,303,981 B2 | 11/2012 | Wallace et al. | |
| 8,357,378 B2 | 1/2013 | Wallace et al. | |
| 2002/0082620 A1* | 6/2002 | Lee | 606/151 |
| 2002/0165337 A1 | 11/2002 | Wallace et al. | |
| 2002/0193448 A1 | 12/2002 | Wallace et al. | |
| 2003/0064109 A1 | 4/2003 | Qian et al. | |
| 2003/0224056 A1 | 12/2003 | Kotha et al. | |
| 2004/0147465 A1 | 7/2004 | Jiang et al. | |
| 2006/0002918 A1* | 1/2006 | Jiang et al. | 424/94.64 |
| 2006/0088518 A1 | 4/2006 | Jorquera Nieto et al. | |
| 2006/0147492 A1 | 7/2006 | Hunter et al. | |
| 2006/0167561 A1 | 7/2006 | Odar et al. | |
| 2006/0204490 A1 | 9/2006 | Pendharkar et al. | |
| 2008/0085316 A1 | 4/2008 | Qian et al. | |
| 2008/0091277 A1 | 4/2008 | Deusch et al. | |
| 2008/0109002 A1 | 5/2008 | Delmotte | |
| 2008/0286376 A1 | 11/2008 | Qian et al. | |
| 2009/0142396 A1 | 6/2009 | Odar et al. | |
| 2010/0028309 A1 | 2/2010 | Odar et al. | |
| 2010/0292717 A1 | 11/2010 | Petter-Puchner et al. | |
| 2010/0318048 A1 | 12/2010 | Hoeffinghoff et al. | |
| 2012/0128653 A1 | 5/2012 | Goessl et al. | |
| 2012/0207813 A1 | 8/2012 | Rhee et al. | |

FOREIGN PATENT DOCUMENTS

| | | |
|---|---|---|
| EP | 0282316 A2 | 9/1988 |
| EP | 0376931 | 7/1990 |
| EP | 0132983 B2 | 12/1991 |
| EP | 0493387 | 7/1992 |
| EP | 0891193 | 1/1999 |
| EP | 0612252 B1 | 5/1999 |
| EP | 1084720 A1 | 3/2001 |
| EP | 1283063 A1 | 2/2003 |
| EP | 1484070 A1 | 12/2004 |
| EP | 1 649 867 A1 | 4/2006 |
| EP | 1414370 B1 | 4/2007 |
| JP | 51-125156 | 11/1976 |
| JP | 59-113889 | 6/1984 |
| JP | 05308969 | 11/1993 |
| JP | 06-254148 | 9/1994 |
| JP | 08-024325 | 1/1996 |
| JP | 9-504719 | 5/1997 |
| JP | 07090241 | 4/2007 |
| KR | 10-1991-0007847 B1 | 10/1991 |
| WO | WO 86/00912 | 2/1986 |
| WO | WO 92/21354 | 12/1992 |
| WO | WO 92/22252 | 12/1992 |
| WO | WO 94/27630 A1 | 12/1994 |
| WO | WO 95/12371 | 5/1995 |
| WO | WO 95/15747 | 6/1995 |
| WO | WO 96/04025 | 2/1996 |
| WO | WO 96/06883 | 3/1996 |
| WO | WO 96/10374 | 4/1996 |
| WO | WO 96/10428 | 4/1996 |
| WO | WO 96/14368 | 5/1996 |
| WO | WO 96/39159 | 12/1996 |
| WO | 97/22371 | 6/1997 |
| WO | 97/37694 A1 | 10/1997 |
| WO | WO 97/37694 A1 | 10/1997 |
| WO | WO 98/08550 A1 | 3/1998 |
| WO | WO 99/13902 A1 | 3/1999 |
| WO | 01/978741 A2 | 12/2001 |
| WO | 02/22059 A1 | 3/2002 |
| WO | WO 02/22184 A2 | 3/2002 |

(56) References Cited

FOREIGN PATENT DOCUMENTS

| WO | WO 02/070594 A2 | 9/2002 |
| WO | WO 03/007845 A1 | 1/2003 |
| WO | WO 2004/108179 A1 | 12/2004 |
| WO | WO 2006/031358 A | 3/2006 |
| WO | WO 2006/118460 A1 | 11/2006 |
| WO | WO 2007/001926 A2 | 1/2007 |
| WO | WO 2007/137839 A2 | 12/2007 |
| WO | WO 2007/137839 A3 | 12/2007 |
| WO | WO 2008/016983 A2 | 2/2008 |

OTHER PUBLICATIONS

Barton et al., "Fibrin Glue as a Biologic Vascular Patch—A Comparative Study" (abstract posted at http://www.ncbi.nlm.nih.gov/ on Jan. 3, 2001 from) *J. Surg. Res.* (1986) 40(5): 510-513.

Baxter product brochure for TissuFleece E, TissuCone E and TissuFoil E (2003).

Baxter Product Catalogue; Collagen; 4 pages (2006).

Boyers et al., "Reduction of Postoperative Pelvic Adhesions in the Rabbit with Gore-Tex Surguical Membrane" *Fert. Ster.* (1988) 49(6):1066--1070.

Bruck, S. D., Ed., Controlled Drug Delivery, CRC Press, Boca Raton, FL (1983) A title page and table of contents.

Cantor et al., "Gelfoam and Thrombin in Gastrointestinal Bleeding: An Experimental Study", pp. 890-893, (Jan. 1950).

Cantor et al., "Gelfoam and Thrombin in Treatment of Massive Gastroduodenal Hemmorhage: A Preliminary Report" *Am J. Surg.* (1950) pp. 883-887.

Cantor et al., "Gelfoam and Thrombin in Treatment of Massive Upper Gastroduodenal Hemorrhage", *Am. J. Surg.* (1951) pp. 230-235.

Chaplin, J.M., et al.; "Use of an Acellular Dermal Allograft for Dural Replacement: An Experimental Study"; Neurosurgery: vol. 45:2; pp. 320-327 (Aug. 1999).

Cheung, David T., et al., "Mechanism of crosslinking of proteins by glutaraldehyde IV: In Vitro and In Vivo stability of a crosslinked collagen matrix", Connective Tissue Research, 1990;25(1), pp. 27-34.

Chuang et al., "Sheath Needle for Liver Biopsy in High-Risk Patients", *Radiology* (1988) 166:261-262.

Collins et al., "Enemata of Gelfoam-Milk Suspension Combined with Thrombin Solution to Control Massive Hemorrhage Following Anorectal Surgery", *Am. J. Proctol.* (1951) 2:60-63.

Collins, Ronald et al., "Use of Collagen Film as a Dural Substitute: Preliminary Animal Studies", Journal of Biomedical Materials Research, vol. 25, 267-276 (1991).

Edgerton et al., "Vascular Hamartomas and Hemangiomos: Classification and Treatment" *Southern Med. J.* (1982) 75(12):1541-1547.

Filippi, R., et al.; "Bovine Pericardium for Duraplasty: Clinical Results in 32 Patients"; Neurosurg. Rev.; vol. 20; pp. 103-107 (2001).

Baxter, "GentaFleece Collagen Fleece—Version 5 : Collagen Sponge with antibiotic protection for surgical use," Retrieved from http://www.advancingbiosurgery.com/en_EU/downloads/ifu_gentafleece.pdf, Mar. 2002, 2 pages. *English portion second column of first page.*

Heller et al., "Release of Norethindrone from Poly(Ortho Esters)" *Polymer Engineering Sci.* (1981) 21:727-731.

Hieb, Lee D. et al., "Spontaneous Postoperative Cerebrospinal Fluid Leaks Following Application of Anti-Adhesion Barrier Gel", SPINE vol. 26, No. 7, pp. 748-751, 2001.

Hood et al., "Efficacy of Topical Hemostat Floseal Matrix in Vascular Surgery," 24th World Congress of the International Society for Cardiovascular Surgery (Sep. 12-16, 1999), 2 pages total.

Hotz et al., "Collagen and Fibrin as Biologic Binders from Granular Hydroxyapatite" (abstract posted at http://www.ncbi.nlm.nih.gov/ on Jan. 3, 2001 from) *Dtsh. Z. Mund. Kiefer Geichtshir.* (1989) 13(4):296-300.

Jeong et al., "Biodegradable Block Copolymers as Injectible Drig-Delivery Systems" *Nature* (1997) 388:860-862.

Jonas, Richard A., et al., "A new sealant for knitted Dacron prostheses: Minimally cross linked gelatin", J. Vasc. Surg., Mar. 1988;7(3), pp. 414-419.

Kim, Kee D., et al., "Reduction in Leg Pain and Lower-Extremity Weakness with Oxiplex/SP Gel for 1 Year after Laminactomy, Laminotomy, and Disectomy", Neurosurg Focus 17 (1): Clinical Pearl 1, Jul. 2004, pp. 1-6.

Kline, D.G.; "Dural Replacement with Resorbable Collagen"; Arch Surg; vol. 91; pp. 924-929 (Dec. 1965).

Knopp, U., "A new collagen foil versus a cadaveric dura graft for dural defects-a comparative animal experimental study", Eans—12th European Congress of Neurosurgery, Lisbon, Sep. 7-12, 2003, 663-666.

Krill et al., "Topical Thrombin and Powdered Gelfoam: an Efficiaent Hemostatic Treatment for Surgery", *J. Tenn. Dent. Assoc.* (1986) 66(2):26-27.

Kuhn, J. et al., "Bilateral Subdural Haemotomata and Lumbar Pseudomeningocele Due to a Chronic Leakage of Liquor Cerebrospinalis after a Lumbar Disectomy with the Application of ADCON-L Gel", J. Neural Neurosurg. Psychiarty 2005; 76: 1031-1033.

Langer et al., "Chemical and Physical Structure of Polymerns as Carriers for Controlled Release of Bioactive Agents: A Review" *Rev. Marco Chem. Phys.* (1983) C23(1):61-126.

Laquerriere, A., et al.; "Experimental Evaluation of Bilayered Human Collagen as a Dural Substitute"; J. Neurosurg; vol. 78; pp. 487-491 (Mar. 1993).

Larson, Paul O., "Topical Hemostatic Agents for Dermatologic Surgery", J. Dermatol. Surg. Oncol., Jun. 1988;14(6), pp. 623-632.

Le, Anh X. et al., "Unrecognized Durotomy After Lumbar Discectomy: A Report of Four Cases Associated with the Use of ADCON-L", SPINE vol. 26, No. 1, pp. 115-118, 2001.

Lee, J.F., et al.; "Experimental Evaluation of Silicone-Coated Dacron and Collagen Fabric-Film Laminate as Dural Substitutes"; J. Neurosurg.; vol. 27; pp. 558-564 (Apr. 1967).

Leong et al., "Polyanhydrides for Controlled Release of Bioactive Agents" *Biomaterials* (1986) 7:364-371.

Leong et al., "Polymeric Controlled Drug Delivery" *Adv. Drug Delivery Rev.* (1987)1:199-233.

Maok, "Hemostatic Agents" (1991) *Today's O.R. Nurse*, pp. 6-10.

Masar et al., "Synthesis of Polyurethanes and Investigation of their Hydrolytic Stability" *J. Polymer. Sci.*, Polymer Symposium (1979) 66:259-268.

Matsumoto, K., et al.; "A Gelatin Coated Collagen-Polyglycolic Acid Composite Membrane as a Dural Substitute"; ASAIO Journal; pp. 641-645 (2001).

Maurer, P.K., et al.; "Vicryl (Polyglactin 910) Mesh as a Dural Substitute"; J Neurosurg; vol. 63; pp. 448-452 (Sep. 1985).

McClure et al., "Massive Gastroduodenal Hemorrhage: Treatment with Powdered Gelfoam and Buffered Thrombin Solution" *Surg.* (1952) 32:630-637.

McPherson, J. M. et al., "An examination of the biologic response to injectable, glutaraldehyde cross-linked collagen implants", J. Biomed. Mater. Res., Jan. 1986;20(1), pp. 93-107.

McPherson, J. M., et al., "The preparation and physiochemical characterization of an injectable form of reconstituted, glutaraldehyde cross-linked, bovine corium collagen", J. Biomed. Mater. Res., Jan. 1986;20(1), pp. 79-92.

McPherson, John M., et al., "The Effects of Heparin on the Physiochemical Properties of Reconstituted Collagen", Coll. Relat. Res., Jan. 1988;8(1), pp. 65-82.

Meddings, N., et al.; "Collagen Vicryl—A New Dural Prosthesis"; Acta Neurochir; vol. 117; pp. 53-58 (1992).

Mello, L.R., et al.; "Duraplasty with Biosynthetic Cellulose: An Experimental Study"; J Neurosurg; vol. 86; pp. 143-150 (Jan. 1997).

Narotam, P.K., et al.; "A Clinicopathological Study of Collagen Sponge as a Dural Graft in Neurosurgery"; J Neurosurg; vol. 82; pp. 406-412 (Mar. 1995).

Narotam, P.K., et al.; "Experimental Evaluation of Collagen Sponge as a Dural Graft"; British Journal of Neurosurgery; vol. 7; pp. 635-641 (1993).

Nimni, M. E., et al., "Chemically modified collagen: A natural biomaterial for tissue replacement", J. Biomed. Mater. Res., Jun. 1987;21(6), pp. 741-771.

(56) References Cited

OTHER PUBLICATIONS

Nimni, Marcel E., "The cross-linking and structure modification of the collagen matrix in the design of cardiovascular prosthesis", J. of Cardiac Surgery, Dec. 1988;3(4), pp. 523-533.
O'Neill, P., et al.; "Use ofPorcine Dermis as Dural Substitute in 72 Patients"; J. Neurosurg.; vol. 61;pp. 351-354 (Aug. 1984).
Palm, S.J., et al.; "Dural Closure with Nonpenetrating Clips Prevents Meningoneural Adhesions: An Experimental Study in Dogs"; Neurosurgery; vol. 45:4; pp. 875-882 (Oct. 1999).
Parizek, J., et al.; "Detailed Evaluation of 2959 Allogeneic and Xenogeneic Dense Connective Tissue Grafts (Fascia Lata, Pericardium, and Dura Mater) Used in the Course of 20 Years for Duraplasty in Neurosurgery"; Acta Neurochir; vol. 139; pp. 827-838 (1997).
Park, Y-K., at al.; "Prevention of Arachnoiditis and Postoperative Tethering of the Spinal Cord with Gore-Tex Surgical Membrane: An Experimental Study with Rats"; Neurosurgery; vol. 42 :4; pp. 813-824 (Apr. 1998).
PCT International Preliminary Report on Patentability and Written Opinion mailed Feb. 17, 2009, International Application No. PCT/US2007/074984, 8 pages.
Pietrucha, K.; "New Collagen Implant as Dural Substitute"; Biomatarials; vol. 12; pp. 320-323 (Apr. 1991).
Pitt et al., "Controlled Release of Bioactive Materials", R. Baker, Ed., Academic Press, New York, 1980.
Porchet, Francois, "Inhibition of Epidural Fibrosis with ADCON-L: Effect on Clinical Outcome One Year Following Re-operation for Recurrent Lumbar Radiculopathy", 1998, pp. 1-10.
Raul, J.S., et al.; "Utilisation du Polyester Urethane (NEURO-PATCH®) Comme Substitut Dural"; Neurochirugie; vol. 49:2-3; pp. 83-89 (2003), *English abstract only on p. 83*.
Raul, J.S., et al.; "Utilisation du Polyester Urethane (NEURO-PATCH®) Comme Substitut Dural"; Neurochirugie; vol. 49:2-3; pp. 83-89 (2003).
Reddy, M., et al.; "A Clinical Study of a Fibrinogen-Based Collagen Fleece for Dural Repair in Neurosurgery"; Acta Neurochir; vol. 144; pp. 265-269 (2002).
Riley et al., "Percutaneous Liver Biopsy with Plugging of Needle Track: A Safe Method for Use in Patients with Impaired Coagulation" *Lancet* (Aug. 25, 1984) pp. 436.
Rosenblatt, Joel, et al., "Effect of electrostatic forces on the dynamic rheological properties of injectable collagen biomaterials", Biomaterials, 1992;13(12), pp. 878-886.
Rosenblatt, Joel, et al., "Injectable collagen as a pH-sensitive hydrogel", Biomaterials, Oct. 1994;15(12), pp. 985-995.
Ross, Jeffrey S. et al., "Association Between Peridural Scar and Recurrent Radicular PAIN After Lumbar Discectomy: Magnetic Resonance Evaluation", Neurosurgery, pp. 855-863, 1996.
Rossler, B., et al., "Collagen microparticles: preparation and properties", J. Microencapsulation, Jan.-Feb. 1995;12(1), pp. 49-57.
San-Galli, F., et al.; "Experimental Evaluation of a Collagen-Coated Vicryl Mesh as a Dural Substitute"; Neurosurgery: vol. 30:3; pp. 396-401 (1992).
Shaffrey, C.I., et al.; "Neurosurgical Applications of Fibrin Glue: Augmentation ofDural Closure in 134 Patients"; Neurosurgery; vol. 26:2; pp. 207-210 (1990).
Sidman et al., "Biodegradable, Implantable Sustained Release Systems Based on Glutamic Acid Copolymers" *J. Membrane Science* (1979) 7:227-291.
Smith, KA, et al.; "Delayed Postoperative Tethering of the Cervical Spinal Corei"; J Neurosurg; vol. 81; pp. 196-201 (Aug. 1994).
Springorum, H.W.; "Die Verwendung von Kollagenfolien zur Uberbruckung von Defekten des Gleitgewebes bei Achillotenotomien und Achillessehnenrupturen"; Akt. Traumatal.; vol. 15; pp. 120-121 (1985), *English abstract only on p. 120*.
Stricker, A., et al.; "Die Verwendung von TissuFoil Membran bei der Sinusbodenaugmentation"; Ellipse; vol. 17:1; pp. 1-5 (2001), *English abstract only on p. 1*.
Sugitachi et al., "A Newly Devised Chemo-embolic Agent, G.T. XIII-ADM." (English abstract posted at http://www.ncbi.nlm.nih.gov/ on Jan. 3, 2001 from) *Gan. To. Kagaku Ryoho*. (1985) 12(10) 1942-1943.
Sugitachi et al., "Locoregional Therapy in Patients with Maignant Pleural Effusion—Two Different Kinds of BAC Therapy" (English abstract posted at http://www.ncbi.nlm.nih.gov/ on Jan. 3, 2001 from) *Gan. To. Kagaku Ryoho*. (1992) 19(10):1640-1643.
Sugitachi et al., "Preoperative Transcatheter Arterial Chemo-embolization for Locally Advanced Breast Cancer: Application for New Thrombotic Materials" *Japan J. Surg*. (1983) 13(5):456-458.
Kofidis, T., et al., "Clinically established Hemostatis Scaffold (Tissue Fleece) as Biomatrix in Tissue- and organ-engineering research", Tissue Eng vol. 9, No. 3, 2003, S.517-523; ISSN: 1076-3279.
TissuFleece E, Version 5, Package Leaflet, Baxter International Inc., 2003, 8 pages, *English portion of instructions for use*.
Tobin et al., "Plugged Liver Biopsy in Patients with Impaired Coagulation" *Digestive Diseases and Science* (1989) 34(1):13-15.
Tucker et al., "Absorbable Gelatin (Gelfoam) Sponge" Charles T. Thomas, Publisher, Springfiled, Illinois, 3-125. 1965.
Vander Salm et al., "Reduction of Sternal Infection by Application of Topical Vancomycin" *J. Thorac. Surg*. (1989) 98:618-622.
Vinas, F.E., et al.; "Evaluation of Expanded Polytetrafluoroethylene (ePTFE) versus Polydioxanone (PDS) for the Repair ofDura Mater Defects"; Neurological Research; vol. 21; pp. 262-268 (Apr. 1999).
Wallace, Donald G., et al., "Injectable cross-linked collagen with improved flow properties", J. of Biomedical Materials Research, Aug. 1989;23(8), pp. 931-945.
Wallace, Donald, "The relative contribution of electrostatic interactions to stabilization of collagen fibrils", Biopolymers, May-Jun. 1990; 29(6-7), pp. 1015-1026.
Warren, W.L., et al.; Dural Repair Using Acellular Human Dermis: Experience with 200 Cases: Technique Assessment; Neurosurgery; vol. 46:6; pp. 1391-1396 (Jun. 2000).
Yuki et al., "Effects of EndoscopicVariceal Sclerotherapy using GT XIII on Blood Coagulation Tests and the Renal Kallikrein-kinin System" (English abstract posted at http://www.ncbi.nlm.nih.gov/ on Jan. 3, 2001 from) *Gastroentral. Japan* (1990) 25(5):561-567.
Ziegelaar, B.W. et al., "The characterisation of human respiratory epithelial cells cultured on reabsorbable scaffolds: first steps towards a tissue engineered tracheal replacement", Biomaterials 23 (2002), 1425-1438; ISSN 0142-9612.
Ziegelaar, B.W.; "Tissue Engineering of a Tracheal Equivalent", Doctoral Thesis at Ludwig Maximilians University, Munich, Germany; 25 pages (2004).
Zins et al., "US-Guided Percutaneous Liver Biopsy with Plugging of the Needle Track: A Prospective Study in 72 High-Rish Patients" *Radiology* (1992) 184(3):841-843.
Gibble, et al., "Fibrin glue: the perfect operative sealant?" Reviews, Transfusion, vol. 30, No. 8, pp. 741-747, 1990.
Guoping, S., et al., "Scaffold Design for Tissue Engineering," Macromolecular Bioscience, pp. 67-77, 2002.
Springorum, H.W., "Die Verwendung von Kollagenfolien zur Uberbruckung von Defekten des Gleitgewebes bei Achillotenotomien und Achillessehnenrupturen," Akt. Traumatol., vol. 15, pp. 120-121, 1985.
Stricker, A., et al., "Die Verwendung von TissuFoil Membran bei der Sinusbodenaugmentation", Ellipse, vol. 17:1, pp. 1-5, 2001.

\* cited by examiner

US 8,940,335 B2

PROCESS FOR MAKING DRY AND STABLE HEMOSTATIC COMPOSITIONS

CROSS REFERENCES TO RELATED APPLICATIONS

This application is a nonprovisional of, and claims the benefit of priority to, U.S. Provisional Patent Application No. 61/350,237 filed Jun. 1, 2010, the entire content of which is incorporated herein by reference for all purposes.

FIELD OF THE INVENTION

The present invention relates to processes for making hemostatic compositions in storage-stable form.

BACKGROUND OF THE INVENTION

Hemostatic compositions in dry storage-stable form that comprise biocompatible, biodegradable, dry stable granular material are known e.g. from WO 98/008550 A or WO 2003/007845 A. These products have been successfully applied on the art for hemostasis. Floseal® is an example for a powerful and versatile haemostatic agent consisting of a granular gelatin matrix swollen in a thrombin-containing solution to form a flow-able paste.

Since such products have to be applied to humans, it is necessary to provide highest safety standards for quality, storage-stability and sterility of the final products and the components thereof. On the other hand, manufacturing and handling should be made as convenient and efficient as possible. If the Hemostatic compositions require a thrombin component for use, provision of this thrombin component in the final product is challenging. Since thrombin and the matrix material usually have different properties concerning manufacture requirements, they have to be manufactured and provided separately. For example, sterilization requirements may differ significantly between relatively stable granular (often also crosslinked) matrix material and proteinaceous components, such as thrombin. Whereas such matrix materials can usually be sterilized by powerful sterilization methods (such as autoclaving, gamma-irradiation, etc.), thrombin (as an enzyme) has to be treated with more care. Those powerful sterilization methods are usually not possible for thrombin, because of loss of enzymatic activity caused by such harsh treatments. For stability reasons, such products (as well as the products according to the present invention) are usually provided in a dry form and brought into the "ready-to-use" form (which is usually in the form of a (hydro-)gel, suspension or solution) immediately before use, necessitating the addition of wetting or solvation (suspension) agents and the mixing of the matrix material component with the thrombin component. Thrombin reconstitution or the mixing step of a thrombin solution with the granular matrix material are steps which usually require some time and handling and can cause problems especially in intensive health care.

It is an object of the present invention to overcome such problems and provide suitable methods for making dry and storage-stable hemostatic composition with are conveniently providable and usable. These methods should provide product formats enabling a convenient provision of "ready-to-use" hemostatic compositions, especially in intensive care medicine wherein the number of handling steps should be kept as low as possible.

SUMMARY OF THE INVENTION

Therefore, the present invention provides a process for making a dry and stable hemostatic composition, said process comprising:

a) providing a dry granular preparation of a biocompatible polymer suitable for use in hemostasis, b) coating the granules in said dry granular preparation with a thrombin preparation, thereby obtaining thrombin coated polymer granules, c) filling said thrombin coated polymer granules into a final container, d) finishing the final container to a storable pharmaceutical device containing said thrombin coated polymer granules as a dry and stable hemostatic composition.

The process provides the dry and stable composition according to the invention in a convenient manner allowing the composition to be easily reconstituted for medical use. The invention further relates to a method for delivering a hemostatic composition to a target site in a patient's body, said method comprising delivering a hemostatic composition produced by the process of the present invention to the target site. According to another aspect, the present invention relates to a finished final container obtained by the process according of the present invention. The invention also relates to a method for providing a ready-to-use hemostatic composition comprising contacting a hemostatic composition produced by the process of the present invention with a pharmaceutically acceptable diluent as well as to a kit comprising the finished final container and other means for applying the composition (e.g. a diluent container). The compositions according to the present invention are particularly useful for providing hemostasis at bleeding sites, including surgical bleeding sites, traumatic bleeding sites and the like. An exemplary use of the compositions may be in sealing the tissue tract above a blood vessel penetration created for vascular catheterization.

DESCRIPTION OF SPECIFIC EMBODIMENTS OF THE INVENTION

The present invention provides an improvement for the delivery and handling of hemostatic compositions, mainly by providing a two-component product in a convenient single-composition format. The hemostatic compositions according to the invention contain coagulation inducing agent coated granules, e.g. thrombin coated granules of a biocompatible polymer suitable for use in hemostasis (the "hemostatic biocompatible polymer component"). Further components may be present. These coated granules may be reconstituted to "ready-to-use" hemostatic preparations using suitable diluents (e.g. aqueous ionic solutions). Preferably, the "ready-to use" preparations are provided as hydrogels. Products of this kind are known in principle in the art, yet in a different format. Usually, the components are provided as separate entities in dry form. Before mixing the components for administration to a patient, the dry components are usually contacted separately with suitable diluents. Mixing of the components is then performed by mixing the separately reconstituted components. For example, a dry thrombin component may be provided which is reconstituted by a pharmaceutically acceptable (aqueous) diluent. The thrombin solution obtained after reconstitution is then used for wetting or solubilizing the polymer, usually under formation of a hydrogel which is then applied to the patient. Since this is at least a two-step process before the product is "ready-to-use", it would be more convenient if a product would necessitate only one step before it is ready to use. However, as stated above, the nature of the two components prevents a simple admixture of the components in the course of the production method, mainly due to stability and activity losses.

With the present invention, production processes are provided which enable that the two components (coagulation inducing agent, e.g. thrombin, and the polymer) are provided already in a combined dry form ready to be reconstituted together. The processes according to the present invention are not only feasible for scientific bench experiments but are suitable for industrial pharmaceutical mass production. With the present invention it is possible to provide this already admixed hemostatic composition without the risk of unwanted degradation or loss of enzyme activity. The resulting compositions have a storage-stability comparable to the previously known products, but are more convenient in handling because separate reconstitution and admixture before medical administration is not necessary with the products obtainable with the present invention. Providing a ready-to-use hydrogel, suspension or solution of the hemostatic composition is possible in a one step process, simply by adding a suitable pharmaceutically acceptable diluent to the composition in the final container. The final container is preferably a syringe designed to directly administer the reconstituted hemostatic composition after contact with the diluent. The thrombin-coated polymer granules according to the present invention can be filled into the syringe, and the syringe can then be closed with the stopper.

The coagulation inducing agent is a substance selected from the group consisting of thrombin, a snake venom, a platelet activator, a thrombin receptor activating peptide and a fibrinogen precipitating agent, preferably it is thrombin.

The "thrombin preparation" can be made from any thrombin preparation which is suitable for use in humans (i.e. pharmaceutically acceptable). Suitable sources of thrombin include human or bovine blood, plasma or serum (thrombin of other animal sources can be applied if no adverse immune reactions are expected) and thrombin of recombinant origin (e.g. human recombinant thrombin); autologous human thrombin can be preferred for some applications. Preferably, the hemostatic composition contains 10 to 100,000 International Units (I.U.) of thrombin, more preferred 100 to 10,000 I.U., especially 500 to 5,000 I.U. The thrombin concentration in the "ready-to-use" composition is preferably in the range of 10 to 10,000 I.U., more preferred of 50 to 5,000 I.U., especially of 100 to 1,000 I.U./ml. The diluent is used in an amount to achieve the desired end-concentration in the "ready-to-use" composition. The thrombin preparation may contain other useful component, such as ions, buffers, excipients, stabilizers, etc. Preferably, the thrombin preparation contains human albumin, mannitol or mixtures thereof. Preferred salts are NaCl and/or $CaCl_2$, both used in the usual amounts and concentrations applied for thrombin (e.g. 0.5 to 1.5% NaCl (e.g. 0.9%) and/or 20 to 80 mM $CaCl_2$ (e.g. 40 mM)).

The "dry granular preparation of a biocompatible polymer" according to the present invention is known e.g. from WO 98/08550 A, however, without a thrombin coating. Preferably, the polymer is a biocompatible, biodegradable dry stable granular material. The "dry" polymer according to the present invention is usually provided with particle sizes of 0.1 to 5,000 μm. Usually, the polymer particles have a mean particle diameter ("mean particle diameter" is the median size as measured by laser diffractometry; "median size" (or mass median particle diameter) is the particle diameter that divides the frequency distribution in half; fifty percent of the particles of a given preparation have a larger diameter, and fifty percent of the particles have a smaller diameter) from 10 to 1000 μm, especially 50 to 500 μm (median size). Applying larger particles is mainly dependent on the medical necessities; particles with smaller mean particle diameters are often more difficult to handle in the production process. The dry polymer is therefore provided in granular form. Although the terms powder and granular (or granulates) are sometimes used to distinguish separate classes of material, powders are defined herein as a special sub-class of granular materials. In particular, powders refer to those granular materials that have the finer grain sizes, and that therefore have a greater tendency to form clumps when flowing. Granulars include coarser granular materials that do not tend to form clumps except when wet. For the present application the particles used are those which can be coated by suitable coating techniques Particle size of the polymer granules according to the present invention can therefore easily be adapted and optimised to a certain coating technique by the becessities of this technique.

A "dry" hemostatic composition according to the present invention has only a residual content of moisture which may approximately correspond to the moisture content of comparable available products, such as Floseal® (Floseal, for example, has about 12% moisture as a dry product). Usually, the dry composition according to the present invention has a residual moisture content below these products, preferably below 10% moisture, more preferred below 5% moisture, especially below 1% moisture. The hemostatic composition according to the present invention can also have lower moisture content, e.g. 0.1% or even below. Preferred moisture contents of the dry hemostatic composition according to the present invention are 0.1 to 10%, especially 0.5 to 5%.

According to the present invention, the hemostatic composition is provided in dry form in the final container. In the dry form, degradation or inactivation processes for the components are significantly and appropriately reduced to enable storage stability. Suitable storage stability can be determined based on the thrombin activity. Accordingly, a dry hemostatic composition of the present kind is storage stable, if no less than 400 I.U./ml (for a 500 I.U./ml product) after reconstitution after 24 months storage in dry form at room temperature (25° C.) are still present (i.e. 80% thrombin activity or more remaining compared to the initial activity before lyophilization). Preferably, the composition according to the present invention has higher storage stability, i.e. at least 90% thrombin activity remaining, especially at least 95% thrombin activity remaining after this 24 months storage.

However, providing a dry mixture of thrombin and a biocompatible polymer is not trivial, because mixture has to be made in the dry form. Mixing the components in the soluble (suspended) form and then beginning the drying process results in intolerable degradation of material. For example, even if thrombin and gelatin are kept at 4° C., a clear degradation is visible after 24 h.

Accordingly, the present invention uses the principle of a coating process to overcome such degradation processes upon mixing. This coating process should prevent a thorough wetting during the contact of thrombin with the polymer which leads to degradation processes. During the coating process, care must be taken that only the outer layer of the polymer granules swell to a certain degree to soak up the desired amount of thrombin. Accordingly, the coating process is preferably carried out by applying thrombin in sprayed form because the wetting state of the polymer granule surface can be easily handled this way. A preferred technique for carrying out the coating process according to the present invention is a fluid bed process. In an fluid bed process or fluid bed coating, the polymer granules are coated with a layer of the proteins contained in the thrombin solution (i.e. preferably human serum albumin and mannitol). In this process the polymer granules are brought into a fluid bed by blowing warm air from underneath through the bed of polymer granules, thereby suspending them in this air stream to create a fluid bed. Into this fluid bed a spray of the thrombin solution is introduced which is intimately mixed with the fluid bed. The spray droplets coat the particles homogeneously with thrombin. This process is carried out at process conditions that retain the activity of thrombin. The outer layer of the polymer granules will likely swell to a certain degree and soak up some of the thrombin solution, while most of the proteins of the thrombin solution will form a layer on the surface of the granules. According to a specifically preferred embodiment, the thrombin preparation introduced in the coating process is obtained by spraying, preferably by aseptic spraying. The spraying can be performed in any spraying apparatus, especially for proteinaceous material, preferably, the apparatuses are sterilized immediately before bringing in the thrombin solution for spraying.

Preferably, the process according to the present invention is carried out in an aseptic environment, especially the coating step and the filling step into the final container should be performed aseptically. It is also preferred to start the process by components which have already been appropriately sterilized and then to perform all further steps aseptically.

A preferred embodiment of the present invention applies the Wurster coating technique. The Wurster process is a coating technique that is well suited to uniformly coat or encapsulate individual particulate materials and is especially popular in pharmaceutical formulation technology. This technology is characterized by the location of a spray nozzle at the bottom of a fluidized bed of solid particles. The particles are suspended in the fluidizing air stream that is designed to induce a cyclic flow of the particles past the spray nozzle. The nozzle sprays an atomized flow of coating solution, suspension, or other coating vehicle (in the present case, the thrombin preparation).

The atomized coating material collides with the particles as they are carried away from the nozzle. The temperature of the fluidizing air is set to appropriately evaporate solution or suspension solvent or solidify the coating material shortly after colliding with the particles.

All coating solids are left on the particles as a part of the developing film or coating. This process is continued until each particle is coated uniformly to the desired film thickness.

The Wurster process is an industry recognized coating technique for precision application of film coat to particulate materials such as powders, crystals, or granules. The technology can be used to encapsulate solid materials with diameters ranging from near 50 μm to several centimeters. The process has a greater drying capacity than other coating systems due to a relatively high fluidizing air velocity. Since the particles actually separate as they are carried away from the nozzle, it is possible to coat small particles without agglomeration. Coating possibilities are relatively unlimited including the ability to place a hydrophilic coat on a hydrophobic core, or a water-based coat on a water-soluble core. Coating properties can be optimized with coat formulation parameters, processing conditions, and layering. A big advantage of fluid bed coating is that can be run as a batch mode technology (Wurster coating). A batch mode technology is very much preferred by manufacturing. With fluid bed coating, particles are fluidized and the coating fluid sprayed on and dried. Small droplets and a low viscosity of the spray medium ensure an even product coating. Preferably, the present coating is carried out as batch fluid bed coating, especially under application of a bottom spray.

The final step of the method is the finishing step. During this step, the final container is appropriately sealed and made ready for storage and/or sale. The finishing step may comprise labeling of the final container, packaging and performing (further) sterilization processes (performed e.g. on the final container or on the packaged product or kit comprising the final container).

Preferably, step d) comprises an EO (ethylene oxide) sterilization step. EO sterilization is common in the present filed of technology. Ethylene oxide gas kills bacteria (and their endospores), mold, and fungi. EO sterilization is used to sterilize substances that would be damaged by high temperature techniques such as pasteurization or autoclaving.

Other preferred embodiments for sterilization are application of ionizing irradiation such as β or γ-irradiation or use of vaporized hydrogen peroxide.

The final container can be any container suitable for housing (and storing) pharmaceutically administrable compounds. Syringes, vials, tubes, etc. can be used; however, providing the hemostatic compositions according to the present invention in a syringe is specifically preferred. Syringes have been a preferred administration means for hemostatic compositions as disclosed in the prior art also because of the handling advantages of syringes in medical practice. The compositions may then preferably be applied (after reconstitution) via specific needles of the syringe or via suitable catheters. The reconstituted hemostatic compositions (which are preferably reconstituted to form a hydrogel) may also be applied by various other means e.g. by a spatula, a brush, a spray, manually by pressure, or by any other conventional technique. Usually, the reconstituted hemostatic compositions according to the present invention will be applied using a syringe or similar applicator capable of extruding the reconstituted composition through an orifice, aperture, needle, tube, or other passage to form a bead, layer, or similar portion of material. Mechanical disruption of the compositions can be performed by extrusion through an orifice in the syringe or other applicator, typically having a size in the range from 0.01 mm to 5.0 mm, preferably 0.5 mm to 2.5 mm. Preferably, however, the hemostatic composition will be initially prepared from a dry form having a desired particle size (which upon reconstitution, especially by hydration, yields subunits of the requisite size (e.g. hydrogel subunits)) or will be partially or entirely mechanically disrupted to the requisite size prior to a final extrusion or other application step. It is, of course evident, that these mechanical components have to be provided in sterile form (inside and outside) in order to fulfill safety requirements for human use.

The dry hemostatic compositions according to the present invention are usually reconstituted (re-hydrated) before use by contacting the dry composition with a suitable diluent. The diluent according to the present invention may be any suitable reconstitution medium for the dry hemostatic composition which allows suitable wetting of the dry composition. Preferably, the dry hemostatic composition is reconstituted into a hydrogel as a "ready-to-use" format.

Suitable diluents are pharmaceutically acceptable aqueous fluids, e.g. pharmaceutical grade de-ionized water (if all ionic or buffer components are already provided in the dry composition; "water-for-injection") or pharmaceutical grade aqueous solutions containing specific ions and/or buffers. These aqueous solutions my further contain comprise other ingredients, such as excipients. An "excipient" is an inert substance which is added to the solution, e.g. to ensure that thrombin retains its chemical stability and biological activity upon storage (or sterilization (e.g. by irradiation)), or for aesthetic reasons e.g. color. Preferred excipients include human albumin, mannitol and sodium acetate. Preferred concentrations of human albumin in the reconstituted product are from 0.1 to 100 mg/ml, preferably from 1 to 10 mg/m. Preferred mannitol concentrations can be in the concentration range of from 0.5 to 500 mg/ml, especially from 10 to 50 mg/ml. Preferred sodium acetate concentrations are in the range of from 1 to 10 mg/ml, especially 2 to 5 mg/ml.

For example, a suitable diluent comprises water for injection, and—independently of each other—NaCl (preferably 50 to 150 mM, especially 110 mM), $CaCl_2$ (preferably 10 to 80 mM, especially 40 mM), human albumin (preferably up to 2% w/w, especially 0.5% w/w), sodium acetate (preferably 0 to 50 mM, especially 20 mM) and mannitol (preferably up to 10% w/w, especially 2% w/w). Preferably, the diluent can also include a buffer or buffer system so as to buffer the pH of the reconstituted dry composition, preferably at a pH of 6.4 to 7.5, especially at pH of 6.9 to 7.1.

In a preferred embodiment, the diluent is provided in a separate container. This can preferably be a syringe. The diluent in the syringe can then easily be applied to the final container for reconstitution of the dry hemostatic compositions according to the present invention. If the final container is also a syringe, both syringes can be finished together in a pack. It is therefore preferred to provide the dry hemostatic compositions according to the present invention in a syringe which is finished with a diluent syringe with a pharmaceutically acceptable diluent for reconstituting said dry and stable hemostatic composition.

The dry granular preparation of a biocompatible polymer suitable for use in hemostasis (the "dry hemostatic polymers") of the present invention may be formed from biologic and non-biologic polymers. Suitable biologic polymers include proteins, such as gelatin, soluble collagen, albumin, hemoglobin, casein, fibrinogen, fibrin, fibronectin, elastin, keratin, and laminin; or derivatives or combinations thereof. Particularly preferred is the use of gelatin or soluble non-fibrillar collagen, more preferably gelatin, and exemplary gelatin formulations are set forth below. Other suitable, biologic polymers include polysaccharides, such as glycosaminoglycans, starch derivatives, xylan, cellulose derivatives, hemicellulose derivatives, agarose, alginate, and chitosan; or derivatives or combinations thereof. Suitable non-biologic polymers will be selected to be degradable by either of two mechanisms, i.e. (1) break down of the polymeric backbone or (2) degradation of side chains which result in aqueous solubility. Exemplary nonbiologic hydrogel-forming polymers include synthetics, such as polyacrylates, polymethacrylates, polyacrylamides, polyvinyl resins, polylactide-glycolides, polycaprolactones, and polyoxyethylenes; or derivatives or combinations thereof. Also combinations of different kinds of polymers are possible (e.g. proteins with polysaccharides, proteins with non biologic hydrogel-forming polymers, etc.)

A non-cross-linked polymer together with a suitable re-hydration aid may be cross-linked in any manner suitable to reconstitute, e.g. to form a suitable hydrogel base. For example, polymeric molecules may be cross-linked using bi- or poly-functional cross-linking agents which covalently attach to two or more polymer molecules chains. Exemplary bifunctional cross-linking agents include aldehydes, epoxides, succinimides, carbodiimides, maleimides, azides, carbonates, isocyanates, divinyl sulfone, alcohols, amines, imidates, anhydrides, halides, silanes, diazoacetate, aziridines, and the like. Alternatively, cross-linking may be achieved by using oxidizers and other agents, such as periodates, which activate side-chains or moieties on the polymer so that they may react with other side-chains or moieties to form the cross-linking bonds. An additional method of cross-linking comprises exposing the polymers to radiation, such as gamma radiation, to activate the polymer chains to permit cross-linking reactions. Dehydrothermal cross-linking methods may also be suitable. Preferred methods for cross-linking gelatin molecules are described below.

According to a preferred embodiment, the biocompatible polymer granulate suitable for use in hemostasis therefore contains a crosslinked polysaccharide, a crosslinked protein, or a crosslinked non-biologic polymer; or mixtures thereof.

As mentioned above, the biocompatible polymer suitable for use in hemostasis is a granular material. This granular material can rapidly swell when exposed to a fluid (i.e. the diluent) and in this swollen form is capable of contributing to a flowable paste that can be applied to a bleeding site. The biocompatible polymer, e.g. gelatin, may be provided as a film which can then be milled to form a granular material. Most of the particles contained in this granular material have preferably particle sizes of 100 to 1,000 µm, especially 300 to 500 µm.

According to a preferred embodiment, the biocompatible polymer suitable for use in hemostasis is a cross-linked gelatin. Dry cross-linked gelatin powder can be prepared to re-hydrate rapidly if contacted with a suitable diluent. The gelatin granules, especially in the form of a gelatin powder, preferably comprises relatively large particles, also referred to as fragments or sub-units, as described in WO 98/08550 A and WO 2003/007845 A. A preferred (median) particle size will be the range from 20 to 1,000 µm, preferably from 100 to 750 µm, especially from 150 to 500 µm, but particle sizes outside of this preferred range may find use in many circumstances. The dry compositions will also display a significant "equilibrium swell" when exposed to an aqueous re-hydrating medium (=diluents). Preferably, the swell will be in the range from 400% to 1000%. "Equilibrium swell" may be determined by subtracting the dry weight of the gelatin hydrogel powder from its weight when fully hydrated and thus fully swelled. The difference is then divided by the dry weight and multiplied by 100 to give the measure of swelling. The dry weight should be measured after exposure of the material to an elevated temperature for a time sufficient to remove substantially all residual moisture, e.g., two hours at 120° C. The equilibrium hydration of the material can be achieved by immersing the dry material in a suitable diluent, such as aqueous saline, for a time period sufficient for the water content to become constant, typically for from 18 to 24 hours at room temperature.

A non-cross-linked gelatin together with the re-hydration aid may be cross-linked in any manner suitable to form a suitable hydrogel base. Dry cross-linked gelatin powders according to this preferred embodiment are preferably obtained by preparing the powders in the presence of certain re-hydration aids. Such re-hydration aids will be present during the preparation of the powders, but will usually be removed from the final products. For example, re-hydration aids which are present at about 20% of the total solids content will typically be reduced to below 1% in the final product, often below 0.5% by weight. Exemplary re-hydration aids include polyethylene glycol (PEG), preferably having a molecular weight of about 1000; polyvinylpyrrolidone (PVP), preferably having an average molecular weight of about 50,000; and dextran, typically having an average molecular weight of about 40,000. It is preferred to employ at least two of these re-hydration aids when preparing the compositions of the present invention, and more particularly preferred to employ all three.

Exemplary methods for producing cross-linked gelatins are as follows. Gelatin is obtained and suspended in an aqueous solution to form a non-cross-linked hydrogel, typically having a solids content from 1% to 70% by weight, usually from 3% to 10% by weight. The gelatin is cross-linked, typically by exposure to either glutaraldehyde (e.g., 0.01% to 0.05% w/w, overnight at 0° C. to 15° C. in aqueous buffer), sodium periodate (e.g., 0.05 M, held at 0° C. to 15° C. for 48 hours), or 1-ethyl-3-(3-dimethylaminopropyl)carbodiimide ("EDC") (e.g., 0.5% to 1.5% w/w overnight at room temperature), or by exposure to about 0.3 to 3 megarads of gamma or electron beam radiation. Alternatively, gelatin particles can be suspended in an alcohol, preferably methyl alcohol or ethyl alcohol, at a solids content of 1% to 70% by weight, usually 3% to 10% by weight, and cross-linked by exposure to a cross-linking agent, typically glutaraldehyde (e.g., 0.01% to 0.1% w/w, overnight at room temperature). In the case of aldehydes, the pH should be held from about 6 to 11, preferably from 7 to 10. When cross-linking with glutaraldehyde, the cross-links are formed via Schiff bases which may be stabilized by subsequent reduction, e.g., by treatment with sodium borohydride. After cross-linking, the resulting granules may be washed in water and optionally rinsed in an alcohol, and dried. The resulting dry powders may then be provided in the final container as described herein.

After cross-linking, at least 50% (w/w) of the re-hydration aid will be removed from the resulting hydrogel. Usually, the re-hydration aid is removed by filtration of the hydrogel followed by washing of the resulting filter cake. Such filtration/washing steps can be repeated one or more additional times in order to clean the product to a desired level and to remove at least 50% of the re-hydration aid, preferably removing at least 90% (w/w) of the re-hydration aid originally present. After filtration, the gelatin is dried, typically by drying the final filter cake which was produced. The dried filter cake may then be broken up or ground to produce the cross-linked powder having a particle size in the desired ranges set forth above.

According to a preferred embodiment, the final container further contains an amount of a stabilizer effective to inhibit modification of the polymer when exposed to the sterilizing radiation, preferably ascorbic acid, sodium ascorbate, other salts of ascorbic acid, or an antioxidant.

According to another aspect, the present invention also provides a method for delivering a hemostatic composition containing the coated granules according to the invention to a target site in a patient's body, said method comprising delivering a hemostatic composition produced by the process according to the present invention to the target site. Although in certain embodiments, also the dry composition can be directly applied to the target site (and, optionally be contacted with the diluent a the target site, if necessary), it is preferred to contact the dry hemostatic composition with a pharmaceutically acceptable diluent before administration to the target site, so as to obtain a hemostatic composition in a wetted form, especially a hydrogel form.

The present invention also refers to a finished final container obtained by the process according to the present invention. This finished container contains the combined components in a sterile, storage-stable and marketable form.

Another aspect of the invention concerns a method for providing a ready-to-use hemostatic composition comprising contacting a hemostatic composition produced by the process according to the present invention with a pharmaceutically acceptable diluent.

The present invention also concerns a kit comprising the dry and stable hemostatic composition according to the present invention in finished form and a container with a suitable diluent. Further components of the kit may be instructions for use, administration means, such as syringes, catheters, brushes, etc. (if the compositions are not already provided in the administration means) or other components necessary for use in medical (surgical) practice, such as substitute needles or catheters, extra vials or further wound cover means. Preferably, the kit according to the present invention comprises a syringe housing the dry and stable hemostatic composition and a syringe containing the diluent (or provided to take up the diluent from another diluent container). Preferably, these two syringes are provided in a form adapted to each other so that the diluent can be delivered to the dry hemostatic composition by another entry than the outlet for administering the reconstituted composition.

The present invention also relates to thrombin coated granules of a biocompatible polymer suitable for use in hemostasis. These coated granules are obtainable by the methods disclosed herein. Preferably, the thrombin coated granules are obtained by fluid bed coating, especially by Wurster coating. According to a preferred embodiment, the granules are thrombin coated gelatin polymers The invention is further described in the examples below and the drawing figure, yet without being restricted thereto.

EXAMPLES

Figure 1:
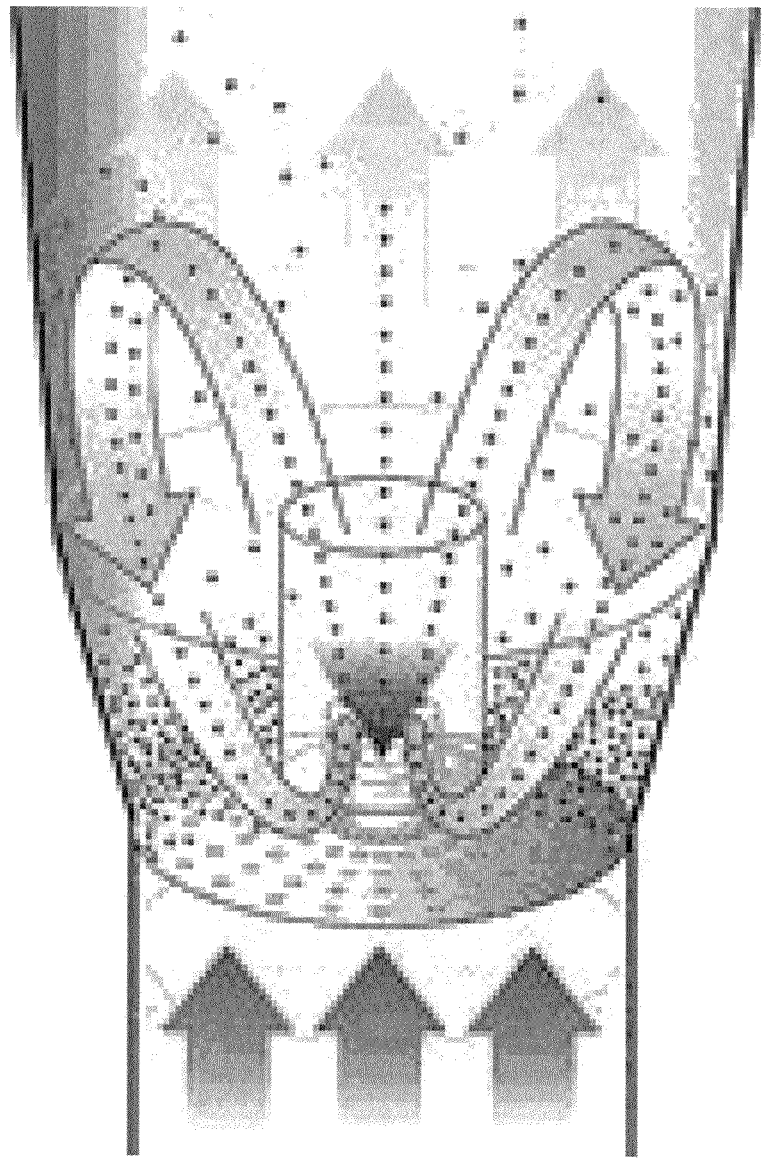
FIG. 1 shows the principle of batch fluid bed coating, bottom spray (Wurster coating).

1. Preparation of the Thrombin Coated Polymer Granules as Dry Hemostatic Composition According to the Present Invention Materials and Methods Equipment MiniGlatt, Wurster, Nitrogen (N2) as process gas, prefiltered through a 0.2 pm filter Mini Glatt Micro-Kit, nozzle 0.5 or 0.8 mm, gap of Wurster partition 10-20 mm, air distribution plate standard, metal filter 2 or 5 µm GPCG 3, 6" Wurster, prefiltered air (0.2 µm), filter PA-CF, air distribution plate P2100, gap of Wurster partition 20 mm Drying Chamber Coating The gelatin granules and the thrombin coated gelatin granules were stored in the refrigerator at 4-8° C. The thrombin solutions (500 IU/ml, 0.9% NaCl; 500 IU/ml, 42 g mannitol/l) were stored in the freezer at −20° C. The process was performed in the Mini Glatt by providing 81 g of gelatin granules; preheating the machine to 37° C.; preheating the solid starting materials to 37±7° C. and holding this temperature during the complete process time. The thrombin solution was sprayed until 400 g solution were applied. Then the coated material was dried for 15 min at the end of the process.

Analytical Methods

Loss on Drying (LOD)

LOD (loss on drying) was determined with a Mettler Toledo Halogen Moisture Analyzer Type HB 43. Drying temperature was 140° C. using a specific stop criterion (<1 mg/60s).

Sieve Analysis

Sieve analysis was performed with a Retsch sieve machine, type AS 200 control g (amplitude: 1.5, time 5 min).

Particle Size Distribution

The particle size distribution was determined in one angle mode using a Laser diffractometer (LD) Malvern Mastersizer 2000 Ver. 5.40. A mass of 10-15 g granule was used in a dry state for the measurement (mean and standard deviation, n=3).

Bulk Density

The measurement of the bulk density was performed in a graduated cylinder with a volume of 100 ml.

Diluent Syringe

The diluent syringe contains an appropriate reconstitution medium for hydrating the product. It is can be coupled with the Floseal syringe either directly or by means of a connector. The diluent is transferred into the Floseal syringe, and the hydrated product is transferred back and forth between the coupled syringes repeatedly to generate a flow-able paste. The diluent syringe can be prepared e.g. by a process such as the following: the medium is sterile filtered and filled in suitable syringes (tike Toppac syringes, Clearshot, . . . ); and, if necessary, end-sterilized by irradiation.

Gelatin Granulate

The gelatin granules bulk manufacturing is performed according to established methods (WO 98/08550 A; WO 2003/00785 A; etc.). The granules ("Floseal" granules; "Floseal" matrix) are immediately sterilized by gamma irradiation. For preclinical sterilization the Floseal matrix is filled into Schott glass bottles of appropriate size.

The required irradiation dose at the current maximum bioburden level (1000 cfu/sample) is 25-40 kGy for the product in the final container. The bulk material is then stored at −20° C. for further manufacturing.

Results

Figure 2A:
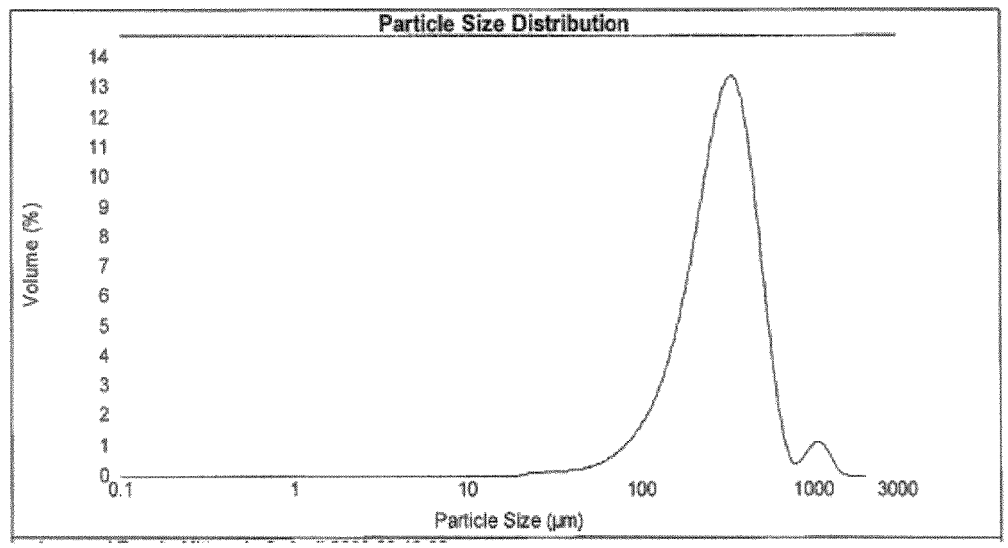
FIG. 2 shows an exemplary particle size distribution of gelatin granules (A) and thrombin coated gelatin granules according to the present invention (B).
Figure 2B:
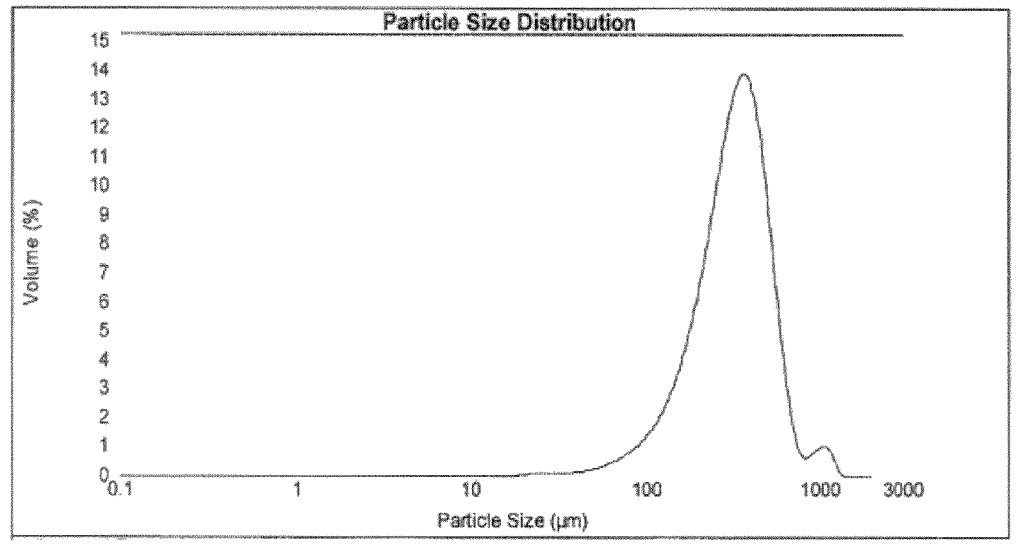

The particle size distribution of the thrombin coated gelatin granule is displayed for an exemplary thrombin coated gelatin granule in FIG. 2 (FIG. 2A shows the gelatin granule before coating (d(0.1)=143.2; d(0.5)=304.3; d(0.9)=517.2); FIG. 2B was obtained with the thrombin solution 500 IU+Mannitol (d(0.1)=155.3; d(0.5)=327.1; d(0.9)=543.0)).

The process was very stable in all experiments performed. The product temperature was adjusted to 36.0±1, 33.0±1 and 39.0±1° C., respectively. The final granule had a good flowability in all batches. High yields above 95% were observed indicating the deposition of the solids from the thrombin solution on the solid starting material. The process vessels looked very clean after the coating steps. There was no material sticking on the wall, only a few larger particles could be seen in the final product. Mean spray rates of 1.64 g/min and 1.24 g/min were applied; amounting to spraying times of 244 min and 323 min, respectively. Lower spray rates usually reduce material loss (thereby increasing yields).

The process could successfully upscaled to the 6" Wurster. Prefiltered air was used as process gas in the GPCG 3 in contrast to the nitrogen in the Mini Glatt. Almost no larger particles were observed in the final product. The material flow was more homogenously in the GPCG 3 compared to the Mini Glatt.

The process humidity was kept low in all processes in order to avoid a swelling and agglomeration of the gelatin. LOD values between 5.4 and 8.3% were determined in the coated granules using a high drying temperature of 140° C. in the halogen moisture analyzer. Mean diameters d(0.5) of 290-327 µm could be determined in the gelatin raw material and for all coated batches. It can be concluded that almost no changes in particle size distribution took place during the coating of the gelatin granule. In total, agglomeration of the gelatin starting material during the process did not occur due to the selected processing conditions.

In summary, the process was proven to be stable in all trials. Product temperatures between 33 and 40° C. could freely be selected. The process was uspcaled from a Mini Glatt to a 6" Wurster. The product quality could be even improved in the larger scale. The particle size distribution of starting gelatine material and processed gelatine was almost unchanged, agglomeration of starting material in a considerable quality was not observed.

2. Stability of the Thrombin Coated Gelatin Granules According to the Present Invention The purpose of this study was to investigate the stability of the fluid bed coated granules obtained in 1., covering 24 months. Specifically, the thrombin coated gelatin granules were tested at 0, 3, 6, 12, 18 and 24 months after preparation; samples were analyzed for equilibrium swell, thromboelastography (TEG; in vitro clotting test) and alpha thrombin.

For this test, thrombin coated gelatin granules which were obtained with the thrombin+mannitol solution were filled in syringes as final containers under aseptic conditions. Finally all syringes were packed and sealed into aluminium-coated bags to prevent absorption of humidity. They were stored at room temperature (22-28° C.). Samples were gathered 0, 3, 6, 12, 18 and 24 months after preparation and analyzed regarding equilibrium swell of the gelatin and alpha thrombin activity. The TEG testing was performed only once after completed preparation (0 month).

No secondary humidity prevention, such as a silica gel desiccant bag, was put into the aluminum-coated bags. To simplify sample collection three syringes were packed and sealed in one aluminum-coated bag, because one determination for equilibrium swell, ect. requires three syringes each.

Buffers and Solutions 0.9% NaCl 9 g NaCl were dissolved in 1000 ml purified water.

40 mM $CaCl_2$ 5.88 g $CaCl_2 \times 2H_2O$ were dissolved in 1000 ml purified water.

Imidazolebuffer 0.7 g Imidazole, 8.8 g NaCl and 4.4 g $CaCl_2 \times 2H_2O$ were dissolved in 800 ml purified water, pH was adjusted to 7.3 with 1 N HCl and finally the total volume of the buffer was filled up to 1000 ml with purified water.

Reconstitution of Stability Syringes

The syringes were reconstituted with 4.0 ml 40 mM $CaCl_2$ solution each as diluent, drawn up into a syringe. The stability syringe and the filled $CaCl_2$ solution syringe were coupled and the contents were mixed by "swooshing" (repeated transfer between the two syringes for a total of 21 passes). The further procedure was dependent on the respective determination.

Equilibrium Swell

The equilibrium swell of gelatin is a parameter that expresses how much fluid the gelatin granules can absorb when incubated in a large excess of fluid within 24 h, relative to their dry weight. It is calculated as "swollen weight/dry weight*100". Statistical calculation for equilibrium swell (Regression, confidence level=CL 95%) was performed with software program "Minitab 15".

TEG

The test was performed by standard manual prescription; Statistical TEG calculations (One-way ANOVA, CL 95%) were performed with software program "Minitab 15".

Alpha Thrombin Recovery/Thrombin Recovery

This test was performed according to established methods using a Kugelkoagulometer.

For the coagulometric determination of thrombin activity (KC4), thrombin has to be extracted from the obtained paste. This was done by weighing in about 1 g of the paste into a 15 ml Falcon tube, adding 10 ml 1M NaCl and shaking the tubes on a wave shaker at 4° C. over night. Next morning the tubes were centrifuged at 4° C. for 10 minutes at 3500 rpm. Then an aliquot of 5 ml from the supernatant was drawn and tested for thrombin activity.

Thrombin recovery (in percent) was normalized to the totally amount of thrombin initially used per g material during preparation of the syringes.

Thrombin was extracted in a 10-fold excess of 1M NaCl (1 ml Floseal paste+10 ml of extraction medium)

To keep the salt concentration as constant between reference and test samples (the test system used is salt dependent) the first dilution of the thrombin reference solution (with which the samples were prepared) was performed in 1M NaCl (1:10, later on 1+10), and the second dilution step of all samples was 1:20 in Imidazolebuffer. The entire dilution factor represented 1:200 (or 1:220, respectively).

At the first two stability points the thrombin starting solutions were diluted 1:400 in Imidazole buffer only. Later on the salt impact on the coagulation time was considered and the starting solutions were diluted as described above. To correct the results of the first stability points the mean value of the starting solutions were used, diluted in 1M NaCl and Imidazole buffer, generated at the subsequent stability points.

Thrombin activity calculated from test solutions diluted in the above manner was the reference value for the calculation of thrombin recovery. For comparative purposes thrombin starting solutions were totally diluted in Imidazole buffer too. The entire dilution factor here was 1:400.

Calculation of Thrombin Recovery:
1. Calculation of Thrombin per g paste [IU/g] in the test samples: (result test sample×dilution×extraction volume)/mass of paste for extraction
2. Calculation total amount of the solid content of granule material and thrombin at the beginning of the test runs: mass of granules+solid contents of thrombin solution The total amount of the solid content is the sum of granule material used for one test run+salt content of the volume of thrombin solution used for the test run
3. Correction for the gelatin volume: mean starting solution× total volume thrombin used for fluid bed coating/total amount of the solid content.
4. Data of sample normalized to data starting solution (salt adjusted): Statistical calculation (regression, CL 95%) was performed with software program "Minitab 15".

Results:

Exemplary results for thrombin recovery are (in %): 72±3 (3 mo); 75±6 (6 mo) and 74±6 (12 mo); according to the statistical analysis of the thrombin recovery, the coated granules tested was to be considered stable.

The thrombin coated gelatin granules were easy to reconstitute all over the whole stability period. The present example showed via thrombin recovery showed that the granules obtained according to the present invention were stable.

3. Effectiveness in the Porcine Liver Abrasion Model

The purpose of this study is to compare the effectiveness of the dry hemostatic composition according to the present invention with an established standard product (Floseal VH S/D; Baxter Healthcare) in the porcine liver abrasion model. Floseal VH S/D is a gelatin matrix that delivers thrombin to stop active bleeding within 2 minutes of application. This product requires a 2-step preparation, (1) reconstitution of thrombin and (2) hydration of the gelatin particles with the reconstituted thrombin. The product according to the present invention is designed to reconstitute the thrombin coated gelatin particles in 1 step and is a major improvement to the 2-step preparation which is unfavorable when the product is needed quickly or in large quantities.

Porcine Liver Abrasion Model

Six female domestic pigs, mean weight of 55.0 kg (range 52.4-58.4 kg), are obtained from Oak Hill Genetics (Ewing, Ill.) and weighed at the time of surgery. Upon arrival, animals are quarantined for 6 days. At the time of surgery, all six pigs show no signs of clinical illness. Ear tags are used to identify animals and cross-referenced to assigned identification numbers. Animals are group housed in pens. Pigs receive water ad libitum and a standard pig diet once daily.

Swine are a well-accepted cardiovascular model and suitable for this type of study. The multiple, large lobes of the liver allowed multiple lesions for direct comparisons of the different test items.

Anesthetics and Fluid Therapy

Pigs are medicated with Midazolam (0.3 mg/kg, IM) and masked-induced with Isoflurane in a 2:1 nitrogen to oxygen carrier. Pigs are intubated and ventilated at a rate of 10-15 breaths per minute. Anesthesia is maintained with Isoflurane in an oxygen carrier. Pigs receive a continuous rate infusion of warmed Lactated Ringer's Solution.

Liver Abrasion Procedure

A porcine liver abrasion model is used for this study. Six pigs are prepared with the goal that 120 lesions (40 per treatment group) are evaluated and sufficient to detect a difference in rates of 80 percent versus 40 percent with $\alpha=0.05$ and power=90%. Each series is confided to either the medial, left lateral or right lateral lobe.

Each lesion series contain three 1 cm diameter, 3-4 mm deep liver abrasions created using a hand drill fixed with sandpaper. Bleeding is assessed and the lesion is randomly and blindly treated with reference or test article. Reference and test article is randomized using a random number generator. Each article is placed onto the lesion, held in place with damp gauze for 2 minutes and blindly assessed for hemostasis 2, 5 and 10 minutes following treatment. Excess reference or test article is irrigated away after the 5 minute assessment.

Heparinization Protocol

A baseline Activated Clotting Time (ACT) is taken and each pig receives a loading dose of heparin, 200 IU/kg. The ACT is assessed every 10 minutes until the ACT is at least 2 times baseline. If the ACT measures less than or near equal to 2 times baseline, the pig was treated with a bolus heparin dose, 75 IU/kg.

Once greater than 2 times baseline, ACT is measured every 20 minutes. If ACT measures less than or near equal to the target 2 times baseline, the pig is given a bolus dose of heparin, 40 IU/kg. If the ACT measures more than the target 2 times baseline, the pig is not treated or given a maintenance bolus dose of heparin, limited to no more than 2,000 IU/hour.

All heparin is given via a peripheral venous catheter. All blood samples are taken from a jugular catheter. Blood pressure and heart rate reference values are recorded at the time of ACT measurements.

Hemostasis Evaluation

Hemostasis is assessed at 0, 2, 5 and 10 minutes after the lesion series is created and treated, where 0 minutes refers to pre-treatment. Scores of 0, 1, 2, 3, 4, and 5 are assigned to no bleeding, ooze, very mild, mild, moderate, and severe; respectively. All three lesions are treated at approximately the same time to avoid difference in location and coagulation that may result from treating each independently. Blood from the lesion is blotted away following each assessment as necessary.

Measurements and Records

The ACT, hemostasis, blood pressure and heart rate are evaluated according to standard methods.

Statistical Analysis

The sampling unit for this study is the liver lesion site with 40 lesions per treatment group for a total of 120 lesions.

Multiple logistic regression is used to evaluate the treatment effect on bleeding score (0=no, 1=ooze, 2=very slight, 3=slight, 4=moderate, and 5=severe) at 2, 5, and 10 minutes post treatment. Independent variables includes treatment group, pig, liver lobe (medial, right or left) and initial bleeding score. The odds ratios for the effects of FB/FS, Lyo/FS, FB/Lyo, and their confidence intervals are computed at each time point post treatment.

The locations of lesions are not evenly distributed across the three lobes and pigs. The lobe effect is found to be not significant, and therefore the analyses are re-performed without this effect. The conclusions are based on the analyses without the lobe effect in the model.

Further Animal Experiments

A preclinical evaluation can be performed to compare in vivo efficacy of the dry hemostatic composition according to the present invention to Floseal VH in a very stringent (highly anti-coagulated) model. This model consists of a 5 mm full-thickness liver puncture with 4 additional incisions radiating from the puncture defect in a cross-wise fashion. 6 animals are used per study group, these animals are heparinized to 4,000 I.U./kg. After the lesion is placed, reconstituted Floseal is applied, and for 2 min light pressure with wet gauze is applied. After this time primary hemostasis after is assessed. If primary hemostasis is not achieved, product is re-applied until hemostasis is achieved, or product (5 ml)/time (15 min) is exhausted. Primary endpoints are achievement of primary hemostasis (Yes/No) and time to hemostasis (min).

If primary hemostasis is achieved, the animals are surgically closed, and after 24 the animals are evaluated for re-bleeding.

The invention claimed is:

1. A process for making a dry and stable hemostatic composition, said process comprising:
    a) providing a dry granular preparation of a biocompatible polymer suitable for use in hemostasis, wherein the biocompatible polymer suitable for use in hemostasis contains a cross-linked gelatin;
    b) coating the granules in said dry granular preparation with a preparation of a coagulation inducing agent, thereby obtaining coagulation inducing agent coated polymer granules, wherein:
        said coagulation inducing agent preparation is a thrombin solution, and
        only an outer layer of the granules swells and soaks up at least some of the thrombin solution upon coating the granules with the preparation of the coagulation inducing agent;
    c) filling said coagulation inducing agent coated polymer granules into a final container; and
    d) finishing the final container to a storable pharmaceutical device containing said coagulation inducing agent coated polymer granules as a dry and stable hemostatic composition, wherein the hemostatic composition has a moisture content below 5%.

2. A process according to claim 1, wherein step b) is performed by a fluid bed process.

3. A process according to claim 1, wherein step d) comprises an ethylene oxide sterilization step.

4. A process according to claim 1, wherein said coagulation inducing agent preparation is a solution containing thrombin in the range of 10 to 10,000 I.U.

5. A process according to claim 1, wherein said coagulation inducing agent preparation is a solution further comprising NaCl and $CaCl_2$.

6. A process according to claim 1, wherein step b) is performed as Wurster coating process.

7. A process according to claim 6, wherein the Wurster coating process is carried out using nitrogen as process gas.

8. A process according to claim 1, wherein a syringe is used as said final container.

9. A process according to claim 8, wherein said syringe is a syringe finished together with a diluent syringe with a pharmaceutically acceptable diluent for reconstituting said dry and stable hemostatic composition.

10. A process according to claim 1, wherein said thrombin solution comprises human thrombin.

11. A process according to claim 1, wherein said biocompatible polymer suitable for use in hemostasis is a granular material.

12. A process according to claim 1, wherein said final container further contains an amount of a stabilizer effective to inhibit modification of the polymer when exposed to sterilizing radiation, and wherein the stabilizer comprises a member selected from the group consisting of ascorbic acid, sodium ascorbate, other salts of ascorbic acid, and an antioxidant.

13. A process according to claim 1, wherein the hemostatic composition in step d) has a moisture content below 1%.

14. A process according to claim 1, wherein the hemostatic composition in step d) has a moisture content below 0.5%.

15. A process according to claim 1, wherein the hemostatic composition in step d) has a moisture content below 0.1%.

16. A process according to claim 1, wherein the biocompatible polymer comprises pellets with a mean particle diameter of 10 to 1000 µm.

17. A process according to claim 1, wherein the biocompatible polymer comprises pellets with a mean particle diameter of 300 to 500 µm.

18. A process according to claim 1, wherein the thrombin solution consists of a thrombin, one or more salts, one or more proteins, mannitol, and water.

19. A process according to claim 1, wherein the thrombin solution consists of a thrombin, one or more salts, mannitol, and water.

* * * * *